(12) United States Patent
Rich et al.

(10) Patent No.: US 11,276,298 B2
(45) Date of Patent: Mar. 15, 2022

(54) PERSONAL ALERT SYSTEM

(71) Applicants: Dan Rich, Rochester, WA (US); Danil Klug, Centralia, WA (US)

(72) Inventors: Dan Rich, Rochester, WA (US); Danil Klug, Centralia, WA (US)

( * ) Notice: Subject to any disclaimer, the term of this patent is extended or adjusted under 35 U.S.C. 154(b) by 0 days.

(21) Appl. No.: 17/039,256

(22) Filed: Sep. 30, 2020

(65) Prior Publication Data

US 2021/0097846 A1 Apr. 1, 2021

Related U.S. Application Data

(60) Provisional application No. 62/908,556, filed on Sep. 30, 2019.

(51) Int. Cl.
| | |
|---|---|
| *G08B 25/01* | (2006.01) |
| *G08B 25/12* | (2006.01) |
| *A61B 5/0205* | (2006.01) |
| *G08B 5/38* | (2006.01) |
| *G08B 25/10* | (2006.01) |

(52) U.S. Cl.
CPC ........ *G08B 25/016* (2013.01); *A61B 5/02055* (2013.01); *G08B 5/38* (2013.01); *G08B 25/10* (2013.01); *G08B 25/12* (2013.01)

(58) Field of Classification Search
CPC ......... H04W 4/00; B60Q 1/00; G08B 25/016; G08B 5/38; G08B 25/10; G08B 25/12; A61B 5/02055
See application file for complete search history.

(56) References Cited

U.S. PATENT DOCUMENTS

| | | | | |
|---|---|---|---|---|
| 7,791,497 | B2* | 9/2010 | Clerk | F21V 33/0076 340/815.4 |
| 2002/0097149 | A1* | 7/2002 | Caplan | B60Q 1/52 340/468 |
| 2002/0105432 | A1* | 8/2002 | Pederson | G09F 21/04 340/815.45 |
| 2008/0239715 | A1* | 10/2008 | Deighton | F21V 17/007 362/183 |
| 2010/0141467 | A1* | 6/2010 | Kirkpatrick | B60Q 1/2611 340/815.45 |
| 2011/0249430 | A1* | 10/2011 | Stamatatos | B60Q 7/00 362/184 |
| 2012/0218101 | A1* | 8/2012 | Ford | G08B 5/22 340/539.12 |

(Continued)

*Primary Examiner* — Nay Tun

(57) ABSTRACT

A system for alerting responders that a person is in need of assistance can include a mounting base, a microcontroller housed within the mounting base, a plurality of light emitting diodes connected between the microcontroller and a power source, a dome coupled to the mounting base, the dome encapsulating the plurality of light emitting diodes and the reflector, a radio frequency receiver housed within the mounting base, a radio frequency transmitter in communication with the radio frequency receiver, in which a signal received by the radio frequency receiver generated from the radio frequency transmitter activates a relay switch electrically coupled to the microcontroller, the microcontroller communicatively coupled to a non-transitory computer readable medium containing computer executable instructions executable to activate at least the plurality of light emitting diodes, and a speaker in communication with the microcontroller.

20 Claims, 2 Drawing Sheets

(56) References Cited

U.S. PATENT DOCUMENTS

| | | | |
|---|---|---|---|
| 2012/0235572 A1* | 9/2012 | Deckard | H05B 47/175 |
| | | | 315/130 |
| 2016/0159446 A1* | 6/2016 | Covelli | G08B 5/36 |
| | | | 340/984 |
| 2016/0277660 A1* | 9/2016 | Kaiser | G03B 17/38 |
| 2019/0156642 A1* | 5/2019 | Royal | H04W 4/029 |
| 2020/0085132 A1* | 3/2020 | Segura | A42B 3/225 |
| 2020/0152024 A1* | 5/2020 | Fitzgerald | B64B 1/40 |

* cited by examiner

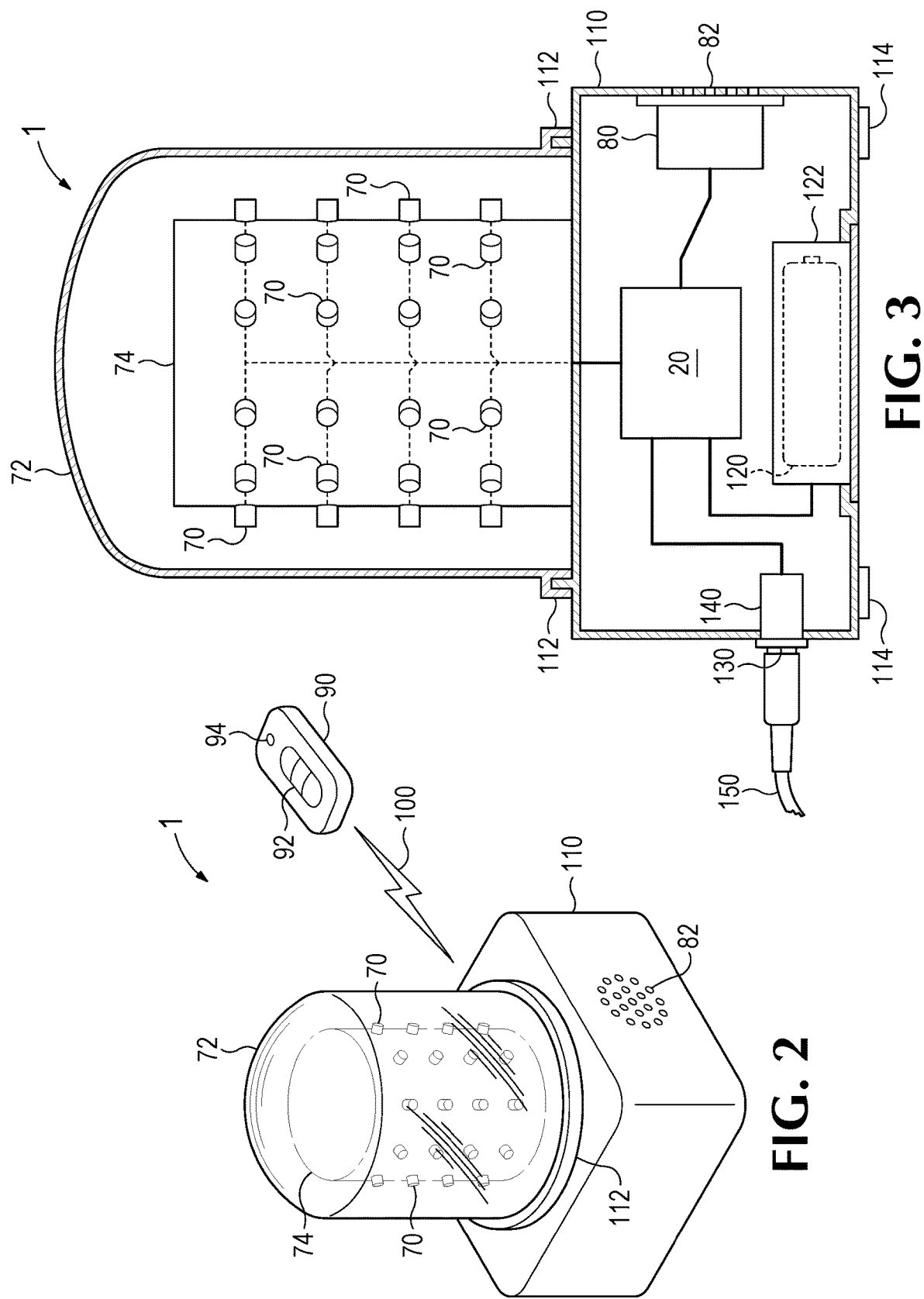

PERSONAL ALERT SYSTEM

CROSS-REFERENCE TO RELATED APPLICATIONS

This application claims the benefit of U.S. Provisional Patent Application No. 62/908,556, filed Sep. 30, 2019, which is incorporated herein by reference in its entirety.

BACKGROUND

This disclosure relates generally to alert notification systems.

In a defined area, such as in and around the home, an alert system to detect emergency conditions may notify emergency response personnel. However, other conditions or situations, while still exigent, but not life-or-death, often do not warrant the hailing of First Responders. Therefore, a person such as a live-in relative, in-home caretaker, or a neighbor or close-proximity relative can be alerted as the primary responder.

SUMMARY

An embodiment of a personal alert system can be a mounting base, a microcontroller housed within the mounting base, a plurality of light emitting diodes operably interconnected to the microcontroller and a power source, in which the plurality of light emitting diodes are coupled to a reflector in perpendicular series forming an array orthogonal to the mounting base of the personal alert system. The embodiment of the personal alert system can include a dome lens coupled to the mounting base, in which the dome lens encapsulates the plurality of light emitting diodes and the reflector, a radio frequency receiver housed within the mounting base, a radio frequency transmitter in operable communication with the radio frequency receiver, in which the signal received by the radio frequency receiver and generated from the radio frequency transmitter activates a relay switch electrically coupled to the microcontroller, the microcontroller communicatively coupled to a non-transitory computer readable medium containing computer executable instructions executable to activate at least the plurality of light emitting diodes, and a speaker in operable communication with the microcontroller. The embodiment of the personal alert system additionally can include that the plurality of light emitting diodes are programmed into at least a flash pattern that appears as if light emitted is rotating within the dome lens.

BRIEF DESCRIPTION OF THE DRAWINGS

FIG. 2 is a perspective view of an embodiment of the personal alert system of FIG. 1;

FIG. 3 is a side view of the personal alert system of FIG. 2.

Corresponding reference numerals indicate corresponding parts throughout the several views of the drawings.

Figure 1:
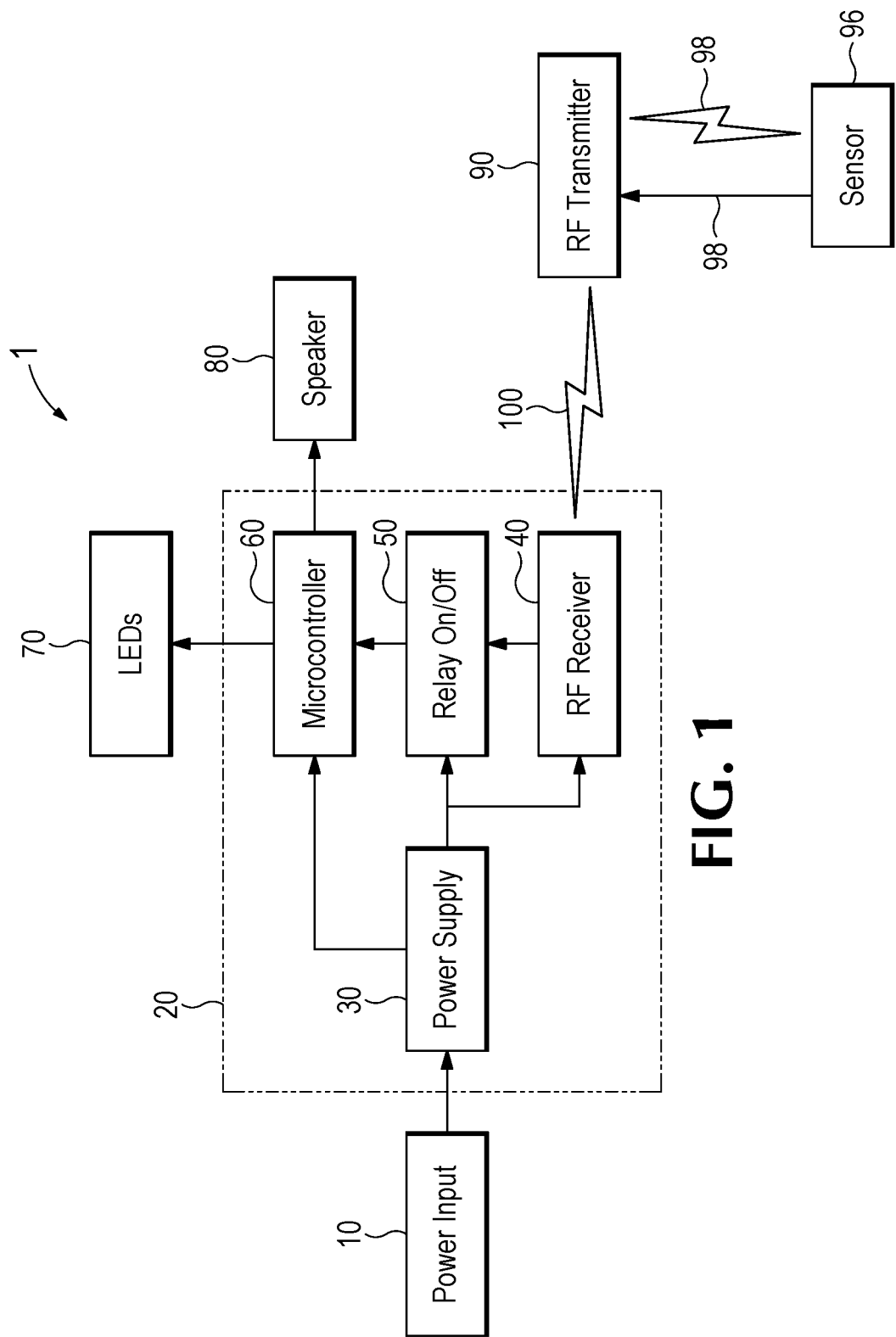
FIG. 1 is a schematic view of a personal alert system, according to the present teachings.

The drawings described herein are for illustrative purposes only of select embodiments and not all possible implementations, and are not intended to limit the scope of the present disclosure.

DETAILED DESCRIPTION

The embodiments in this disclosure, as illustrated in FIGS. 1 through 3 and described in the text below, are adapted for health and personal care in the home or retirement community, and may be used in assisted living facilities. Responders can include a caretaker such as a nurse, and/or a person such as a live-in relative, in-home caretaker, or a neighbor or close-proximity relative, who for example, lives next door to the user.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation. Moreover, it is to be appreciated that the drawings may not be to scale.

With reference primarily to FIG. 1, a personal alert system 1 is depicted. The personal alert system 1 includes power input 10 and control circuit 20. Control circuit 20 includes power supply 30, radio frequency receiver 40, relay on/off 50, and microcontroller 60. Also included within the personal alert system 1 are light emitting diodes 70, speaker 80, radio frequency transmitter 90, and signal 100.

Power input 10 of the personal alert system 1 can be an AC input or battery power input not to exceed 24 volts. In an embodiment, the power input 10 can be a 12V DC input from an AC adapter, 12 volts from an automotive adapter, rechargeable 12V battery, or DC 5V to DC 12V USB. The illustrative examples of the power input 10 of the personal alert system 1 are not intended to preclude embodiments which incorporate similar or equivalent AC inputs, battery inputs, or USB inputs, currently or prospectively available.

Control circuit 20 of the personal alert system 1 includes power supply 30. Power supply 30 can be a voltage converter typically used in LED display applications. An example of a commercially available power supply 30 is the Fulree DC 12V to DC 5V non-isolated step-down voltage converter having 15 W output power. The illustrative and commercially available examples of the power supply 30 of the personal alert system 1 are not intended to preclude embodiments which incorporate similar or equivalent voltage converters, currently or prospectively available.

The personal alert system 1 incorporates a radio frequency receiver 40 and a relay on/off 50 within the control circuit 20. A portable radio frequency transmitter 90 accompanies the radio frequency receiver 40, transmitting signal 100 from the transmitter 90 to the receiver 40. An example of a commercially available radio frequency receiver 40 with transmitter 90 is the eMylo RF Wireless Remote Control Switch having a remote control distance ranging between 30 meters to 50 meters. In another embodiment, the remote control distance can be up to 100 meters. In yet another embodiment the radio frequency receiver 40 with transmitter 90 can be a transceiver to exchange communications and data with remote computers and other mobile devices. The illustrative and commercially available examples of the radio frequency receiver 40 with radio frequency transmitter 90 and relay on/off 50 of the personal alert system 1 are not intended to preclude embodiments which incorporate similar or equivalent wireless transceivers, input/output ports, counters, interrupters or re-interrogators, and other transponders, currently or prospectively available.

The microcontroller 60 of the personal alert system 1 can be a chip and integrated circuit board with a processor and memory communicatively coupled to a non-transitory computer readable medium containing computer-executable instructions, and a bootloader that allows the uploading of new code to the microcontroller 60 without the use of an external hardware programmer. The microcontroller 60 can also include SRAM and an EEPROM, which can be read and written with the EEPROM library. An example of a commercially available microcontroller 60 is the Elegoo EL-CB-001 UNO R3 Board with the ATMEGA 16U2 chip. The illustrative and commercially available examples of the microcontroller 60 of the personal alert system 1 are not intended to preclude embodiments which incorporate similar or equivalent processors, memory devices or storage devices, controllers, and timers, currently or prospectively available.

Referring primarily now to FIGS. 1, 2, and 3, light emitting diodes 70 can simulate the rotating pattern commonly associated with emergency vehicle lights. A reflector 74 can be used to frame individual light emitting diodes 70 or light emitting diodes 70 in series such that the light emitting diodes 70 are disposed in columns and rows on the outfacing wall of the reflector 74. The reflector 74 can be hexagonal, pentagonal, rectangular, round, square or any other shape. In an embodiment, the light emitting diodes 70 can be fashioned into strips. Each strip of light emitting diodes 70 can be vertically disposed within the reflector 74 and can be orthogonal to the mounting base 110, which is described below.

With continuing reference primarily to FIGS. 1, 2, and 3, the personal alert system 1 can include a speaker 80 and a speaker grill 82 to implement a programmable, auditory alert to complement or in lieu of the visual alert beacon of the activated light emitting diodes 70. The volume of the speaker 80 of the personal alert system 1 can, but not necessarily, be adjusted manually/automatically by slider control sensor(s) or button(s) or by using voice commands (voice activated) or by using any of the push-buttons 92 which are used to initiate an alarm call once the alarm has been activated.

Now with primary reference to FIGS. 2-3, dome lens 72 encapsulates the light emitting diodes 70, reflector 74, and associated wiring connection from the control circuit 20 to the light emitting diodes 70. The dome lens 72 can be transparent or translucent and can, but not necessarily, be amber, red, blue, green and clear or multi-color, depending on the desired effect of the emitted light acting as a beacon. The dome lens 72 can be shaped as a fluted dome, cylindrical or fluted cylindrical. Besides acting as a personal alert beacon, the dome lens 72 can additionally be used to warn others of hazardous conditions, increase visibility or bring attention to any important area or function.

With continuing reference primarily to FIGS. 1, 2, and 3, radio frequency transmitter 90 includes a panic push-button 92 and a light emitting diode 94 which may emit light when the panic push-button 92 is activated. The signal 100 from radio frequency transmitter 90 is received by the radio frequency receiver 40 for activation of the light emitting diodes 70. The light emitting diode 94 of the radio frequency transmitter 90 is off when the panic push-button 92 has not been activated and therefore, the personal alert system 1 has not been activated, either. The signal 100 may also communicate with a device such as a telephone or smart phone. The signal 100 may include AM (amplitude modulation), FM (Frequency Modulation) (in all its forms), Phase Modulation (in all its forms), broad spectrum or 'Bluetooth' technology, or other forms of wireless transmission technology.

The panic push-button 92 of the radio frequency transmitter 90 can, but not necessarily, be slightly recessed. The panic push-button 92 can also but not necessarily have a protective rim to prevent accidental activation. The panic push-button 92 can, but not necessarily, be covered by a protective cover to prevent accidental activation.

In an embodiment of the personal alert system 1, the panic push-button 92 with radio frequency transmitter 90 can be worn on a user's clothing or body, in which the radio frequency transmitter 90 transmits signal 100 to radio frequency receiver 40 of the personal alert system 1. A user display 94 can, but not necessarily, be used to display signal 100 status, indicating when the signal 100 has been transmitted to the radio frequency receiver 40 of the personal alert system 1.

In an embodiment, the radio frequency transmitter 90 of the personal alert system 1 is small, lightweight, and portable so as to prevent obstructing the user's freedom of movement. The radio frequency transmitter 90 can, but not necessarily, be a wrist band, watch or pendant. The personal alert system 1 can include a portable housing which may be designed and manufactured for a responder on the move so that it may be carried as a pager, or worn as a pendant, or on a belt key fob.

With reference primarily again to FIGS. 2-3, mounting base 110 can house the internal electronics including control circuit 20 of the personal alert system 1. Speaker 80 can, but not necessarily, be housed within the mounting base 110. Mounting base 110 can, but not necessarily, be manufactured from acrylonitrile-butadiene-styrene ("ABS"), and other common plastics. Mounting base 110 can be made from 3-D printing materials, including a 3-D printer and other additive manufacturing machines and processes.

Still with reference primarily to FIGS. 2-3, mounting base 110 includes couplers 112 for engaging the dome lens 72 to the mounting base 110. Couplers 112 can be a threadable engagement configuration, snap-to-fit coupling, and a fastener or fasteners. The illustrative examples of the attachment 112 of the personal alert system 1 are not intended to preclude embodiments which incorporate similar or equivalent fasteners or fastening device, currently or prospectively available.

The personal alert system 1 can, but not necessarily, include platforms 114 for setting the mounting base atop a fixture within the home or garage or just outside of the home or garage, for example.

The personal alert system 1 can, but not necessarily, be powered from a disposable/rechargeable battery 120 and mounting base 110 can include a battery storage compartment 122 for housing the battery or batteries 120.

The mounting base 110 can, but not necessarily, be placed into an independent charging unit which is part of the personal alert system 1 via suitable electrical contacts provided on or within the mounting base 110 and independent charging unit.

With reference primarily to FIG. 3, the mounting base 110 of the personal alert system 1 can, but not necessarily, be powered or recharged by an AC adapter having a cord 150 for entering port 130 of the AC outlet 140 of the mounting base 110.

In an embodiment of the personal alert system 1, the personal alert system 1 can be powered via solar energy. When stationing the personal alert system 1 outdoors, solar panels, such as four, separate solar panels can be attached to the dome lens 72, for example. The solar panels can, but not necessarily, be configured in a trapezoidal fashion as having a slope in series within one another for allowing rain, snow, and other precipitation to not accumulate on top of the personal alert system 1.

In an embodiment of the personal alert system 1, features of the system 1 for housing internal controls can, but not necessarily, be weatherproof and waterproof.

In an embodiment of the personal alert system 1, mounting base 110 can, but not necessarily, include magnets for attaching the personal alert system 1 where desired.

In an embodiment of the personal alert system 1, the radio frequency transmitter 90 can include a medical sensor or body sensor 96 electrically coupled to or in operable communication 98 with the radio frequency transmitter 90 or the microcontroller 60. The sensor can, but not necessarily, sense vital signs such as pulse, temperature, or oxygen saturation levels, in which the radio frequency transmitter 90 can activate the system 1 in response to abnormal vital signs.

In an embodiment of the personal alert system 1, an interface for viewing short circuit video can access a camera nearest the user who activates the system 1 via a button or switch for receiving the user's distress or alarm notification. The interface can also include a voice receiver for receiving the user's voice instructions. The interface can incorporate data from one or more sensors 96 for sensing the physical condition of the user. These sensing devices 96 can, but not necessarily, be blood pressure sensors, temperature sensors, heart rate sensors, oxygen sensors or any other suitable monitoring devices for sensing vital signs.

The personal alert system 1 can, but not necessarily, be provided locally, in the vicinity of the user, such as in the user's house.

In an example, the personal alert system 1 is installed in the living room of the home with the transmitter/panic button 90, 92 within reaching distance of the user who is in the bedroom or bathroom, for instance. When activated, the personal alert system 1 can provide another sensory indicator for a responder in the living room who may, for example, have turned up the television volume making it difficult to hear the user's voice in the next room.

In an example, the personal alert system 1 is installed outside the garage door. The responder, while mowing the lawn, can visibly see the visual alert of the system 1 despite the noise of the lawn mower.

In an embodiment of the personal alert system 1, the system 1 can be formed by a telephone network and more in particular by a mobile telephone network. For example, if the user is not too far removed from a telephone network receiver, the transmitter of the personal alert system 1 can directly dial a phone number.

In an embodiment of the personal alert system 1, the system 1 can, but not necessarily, include a sound receiving device in the form of a microphone or a sound producing device in the form of a speaker 80. This provides a true two way conversation between the user and the responder, or in the case of an emergency, between the user and Call 911 services.

In an embodiment of the personal alert system 1, the user's speech may be digitized and then converted from a digital speech signal to an analog speech signal.

In an embodiment of the personal alert system 1, the personal alert system 1 can, but not necessarily, be programmed to remotely operate other appliances such as doorbells, smart phones, smoke detectors, alarm systems and other domestic systems that can alert a deaf person, so long as those devices have a transmitter/transceiver operating on the same frequency and own identity code, to identify that unit.

In an embodiment of the personal alert system 1, the system 1 can be connectable to a telephone line and capable of dialing one or more emergency numbers of priority thereby dialing a first telephone number and if no connection is made to the first number, then dialing a second number and so on.

In an embodiment of the personal alert system 1, geofencing or range monitoring for monitoring the distance between the responder and the personal alert system 1 and/or the user and the personal alert system 1. If, for example, the system 1 detects that the personal alert system is approaching the maximum allowable distance, the user and/or responder, depending on which of the two or, if both are being monitored, can be informed of this. The system 1 can monitor the signal strength of the signal of the personal alert system 1 and if the signal is too weak, the system can inform the user that the personal alert system 1 is out of range.

In an embodiment of the personal alert system 1, the system 1 can contact additional designated responders to help to inform them that the distance between the first designated responder and the user is out of range. This feature can be useful in psychiatric hospitals, prisons and probation centers.

In an embodiment of the personal alert system 1, the system 1 can include location technology, such as global positioning system ("GPS") or similar global wireless positioning equipment/software, which allow any responder to be able to locate the user anywhere in the world.

In an embodiment of the personal alert system 1, the system 1 can be designed such that it may connect to or communicate with both domestic and commercial security alarm systems, and associated peripherals such as passive infra-red devices, pull cords, smoke detectors, doors, cameras etc., medical monitoring equipment and other ancillary equipment such that relevant data from these systems/accessories can also be sent either manually or automatically to a dedicated number or responder, programmed 60 by either the user installer/manufacturer or end user.

The present teachings thus advantageously provide for an alert system 1 that allows responders to attend to person in need. The present teachings provide for numerous other advantages as well, as will be recognized by one skilled in the art.

The description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used is for the purpose of describing particular example embodiments only and is not intended to be limiting. The singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section could be termed a second element, component, region, layer or section without departing from the teachings of the example embodiments.

Spatially relative terms, such as "inner," "outer," "beneath," "below," "lower," "above," "upper," and the like, may be used for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It is understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, quadrants, thirds, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 routes refers to groups having 1, 2, or 3 routes. Similarly, a group having 1-5 impact zones refers to groups having 1, 2, 3, 4, or 5 impact zones and more or less, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

What is claimed is:

1. A personal alert apparatus, comprising:
a mounting base;
a microcontroller housed within the mounting base;
a plurality of light emitting diodes operably interconnected to the microcontroller and a power source, the plurality of light emitting diodes coupled to a reflector in perpendicular series forming an array orthogonal to the mounting base;
a dome lens coupled to the mounting base, the dome lens encapsulating the plurality of light emitting diodes and the reflector;
a radio frequency receiver housed within the mounting base;
a radio frequency transmitter in remote operable communication with the radio frequency receiver, wherein a signal received by the radio frequency receiver generated from the radio frequency transmitter activates a relay switch electrically coupled to the microcontroller; and
a speaker in operable communication with the microcontroller,
wherein the microcontroller communicatively coupled to a non-transitory computer readable medium containing computer executable instructions executable to activate at least the plurality of light emitting diodes,
wherein the personal alert apparatus removably attached to an object to allow the personal alert system to be in plain view of a responder.

2. The personal alert apparatus of claim 1, wherein the computer executable instructions are further executable to program the plurality of light emitting diodes into at least a flash pattern.

3. The personal alert apparatus of claim 1, wherein the signal received by the radio frequency receiver generated from the radio frequency transmitter originates by user activation of a push-button housed within the radio frequency transmitter.

4. The personal alert apparatus of claim 1, comprising one or more sensors in operable communication with the radio frequency transmitter to detect pulse rate, blood pressure, temperature, and oxygen saturation levels.

5. The personal alert apparatus of claim 1, comprising the one or more sensors communicatively coupled with the microcontroller.

6. The personal alert apparatus of claim 1, wherein the signal received by the radio frequency receiver generated from the radio frequency transmitter originates from the one or more sensors.

7. The personal alert apparatus of claim 1, further comprising a transceiver for exchanging data with a remote computing device.

8. The personal alert apparatus of claim 7, wherein the computer executable instructions are further executable via the transceiver to communicatively couple to a smart phone, a doorbell system, a smoke detector system, and a home alarm system.

9. A personal alert system, comprising:
a mounting base;
a microcontroller housed within the mounting base;
a beacon operably interconnected to the microcontroller and a power source, the beacon comprising a plurality of light emitting diodes, the plurality of light emitting diodes coupled to a reflector in perpendicular series forming an array orthogonal to the mounting base;
a radio frequency receiver housed within the mounting base;
a radio frequency transmitter in remote operable communication with the radio frequency receiver, wherein a signal received by the radio frequency receiver generated from the radio frequency transmitter activates a relay switch electrically coupled to the microcontroller; and
a speaker in operable communication with the microcontroller,
wherein the microcontroller communicatively coupled to a non-transitory computer readable medium containing computer executable instructions executable to activate at least the beacon,
wherein the personal alert apparatus removably attached to an object to allow the personal alert system to be in plain view of a responder.

10. The personal alert system of claim 9, wherein the beacon comprises:
a dome lens coupled to the mounting base, the dome lens encapsulating the plurality of light emitting diodes and the reflector.

11. The personal alert system of claim 10, wherein the computer executable instructions are further executable to program the plurality of light emitting diodes into at least a flash pattern.

12. The personal alert system of claim 9, wherein the signal received by the radio frequency receiver generated from the radio frequency transmitter originates by user activation of a push-button housed within the radio frequency transmitter.

13. The personal alert system of claim 12, comprising one or more sensors in operable communication with the radio frequency transmitter to detect pulse rate, blood pressure, temperature, and oxygen saturation levels.

14. The personal alert system of claim 13, comprising the one or more sensors communicatively coupled with the microcontroller.

15. The personal alert system of claim 14, wherein the signal received by the radio frequency receiver generated from the radio frequency transmitter originates from the one or more sensors.

16. The personal alert system of claim 9, further comprising a transceiver for exchanging data with a remote computing device.

17. The personal alert system of claim 16, wherein the computer executable instructions are further executable via the transceiver to communicatively couple to a smart phone, a doorbell system, a smoke detector system, and a home alarm system.

18. A method of using a personal alert system, comprising:
removably attaching the personal alert system to an object, wherein at least a beacon of the personal alert system disposed in plain view of a responder, the beacon comprises a plurality of light emitting diodes, the plurality of light emitting diodes coupled to a reflector in perpendicular series forming an array orthogonal to a mounting base;
causing to generate a remote signal from a radio frequency transmitter in response to a user;

receiving the remote signal transmitted from the radio frequency transmitter;

activating a relay switch coupled to a microcontroller communicatively coupled to a non-transitory computer readable medium containing computer executable instructions executable to activate the beacon;

sensing, by the responder, the beacon; and responding to the user.

19. The method of claim 18, further comprising activating a speaker.

20. The method of claim 18, wherein the beacon comprises a dome lens coupled to the mounting base, the dome lens encapsulating the plurality of light emitting diodes and the reflector.

* * * * *